United States Patent [19]

Grollier et al.

[11] Patent Number: 4,871,530
[45] Date of Patent: Oct. 3, 1989

[54] AQUEOUS DELAYED-FOAMING COSMETIC COMPOSITION FOR HAIR AND SKIN TREATMENT

[75] Inventors: Jean F. Grollier, Paris; Claude Dubief, Le Chesnay; Daniele Cauwet, Paris, all of France

[73] Assignee: L'oreal, Paris, France

[21] Appl. No.: 28,133

[22] Filed: Mar. 19, 1987

[30] Foreign Application Priority Data

Mar. 19, 1986 [LU] Luxembourg .................... 86361

[51] Int. Cl.$^4$ .................... A61K 7/075; A61K 7/15; A61K 7/11; A61K 7/50
[52] U.S. Cl. ........................ 424/47; 424/70; 424/73; 424/71; 252/DIG. 13
[58] Field of Search .................... 424/47, 70, 71, 73, 424/DIG. 1; 252/DIG. 13; 514/54, 61, 944, 945; 536/114, 123

[56] References Cited

U.S. PATENT DOCUMENTS

| | | | |
|---|---|---|---|
| 3,541,581 | 11/1970 | Monson | 252/90 |
| 4,329,448 | 5/1982 | Cox et al. | 536/114 X |
| 4,454,316 | 6/1984 | Veeder et al. | 536/123 |
| 4,495,169 | 1/1985 | Schmolka | 424/47 |
| 4,591,610 | 5/1986 | Grollier | 524/55 |

FOREIGN PATENT DOCUMENTS

| | | | |
|---|---|---|---|
| 1167215 | 11/1958 | France. | |
| 2136689 | 9/1984 | United Kingdom | 424/70 |
| 2164558 | 3/1986 | United Kingdom | 424/70 |
| 2166150 | 4/1986 | United Kingdom | 424/73 |

Primary Examiner—Ellis P. Robinson
Assistant Examiner—Susan S. Rucker
Attorney, Agent, or Firm—Fleit, Jacobson, Cohn, Price, Holman & Stern

[57] ABSTRACT

A cosmetic composition suitable for the treatment of the hair or of the skin in the form of a delayed-foaming gel, which comprises, in a cosmetically acceptable aqueous medium, at least one surface-active agent, at least one heterobiopolysaccharide and at least one delayed-foaming agent which is able to form a foam after the composition is spread on the hair or the skin.

30 Claims, No Drawings

AQUEOUS DELAYED-FOAMING COSMETIC COMPOSITION FOR HAIR AND SKIN TREATMENT

The present invention relates to a cosmetic composition for hair and skin treatment, packaged in a device under pressure and forming a delayed-foaming gel.

Gelled delayed-foaming compositions are well known in the field of cosmetics. These compositions, which take the form of gels, generally include, in combination with active substances which are to be dispensed, a delayed-foaming agent which is in the liquid-vapour state at the temperatures of use under a relatively reduced pressure of the order of a few bars.

A composition in the form of delayed-foaming gel is the name given to a composition packaged under pressure in an aerosol device, which is delivered, under the effect of a propellant, in the form of a nonfoaming gel under static conditions but which, under the mechanical action due to the spreading, generates a foam "in situ" on the hair or on the skin.

Cosmetic compositions in the form of delayed-foaming gels which are known in the state of the art are aqueous and generally contain a foaming agent which is called "delayed", in the presence of a thickening agent such as carboxymethyl cellulose, methyl cellulose, hydroxyethyl cellulose, hydroxypropyl cellulose, a copolymer of acrylic acid and polyallyl sucrose or polyoxyalkylenes or polyethylene glycol ethers.

There are also known anhydrous self-foaming compositions described in particular in Canadian Patent Nos. 1,028,957, No. 1,029,306 and No. 1,021,264.

These compositions of the state of the art and containing, more particularly, the abovementioned thickening agents have a number of disadvantages. It has been found, in fact, that these compositions presented problems of preservation of the self-foaming capacity during storage and especially after an initial use of a part of the product packaged as an aerosol. This appears to be due to the fact that the so-called delayed-foaming agent separates out at the surface, and this leads to a phase separation and a major loss of this foaming agent when the product is first used. It is then found that the self-foaming property under the mechanical action due to the spreading is diminished or disappears.

To overcome this type of problem, some compositions of the prior art have been dispensed from an aerosol device with a diaphragm as described in U.S. Pat. No. 3,541,581, in which compositions the active ingredients containing the foaming agent are separated from the propellant by means of an extensible diaphragm. In this case, an intimate contact between the active agents and the delayed-foaming agent must be produced by preliminary mixing of the two components under pressure.

Furthermore, the applicant has tried to use, in such compositions, cationic compounds which are known per se in the cosmetics industry for skin or hair treatment. These compounds make it possible, in particular, to impart good disentangling properties to hair and softness to the skin. It has found that it was impossible to produce a stable and homogeneous mixture by combining, in a gelled and aqueous delayed-foaming composition, the abovementioned thickening agents for producing a gel with a cationic compound and a delayed-foaming agent. The foaming agent separates out at the surface and the remaining composition flows out as several phases, and this leads to the formation of a gel which does not possess the desired self-foaming properties.

The applicant has found, surprisingly, that by employing a water-soluble heterobiopolysaccharide, the best known example of which is xanthane gum, in these compositions, it was possible to overcome the abovementioned disadvantages and to prepare, under good conditions, delayed-foaming compositions in the form of an aqueous gel, preserving their delayed-foaming properties during their storage, even after a first use.

Although this explanation is not intended to imply any limitation, this result appears to be due essentially to the fact that the heterobiopolysaccharide absorbs the delayed-foaming agent completely and immediately and consequently prevents it from separating out.

This effect is especially remarkable in the case of the compositions which additionally contain cationic compounds for hair or skin treatment. These compositions are, in fact, homogeneous and stable, in contrast to what it was possible to produce previously.

The compositions according to the invention have the advantage, furthermore, of being capable of being prepared directly in the aerosol packaging, avoiding the intermediate stage required in the previous processes to promote the distribution of the delayed-foaming agent in the composition by a preliminary mixing under pressure.

By virtue of the composition according to the invention, the delayed-foaming gel can be prepared directly by introducing the delayed-foaming agent into the aerosol device containing a diaphragm, that is to say a jacket, following the introduction of the gelling agent and of other active substances such as the surface and treatment agent. The compositions according to the invention have the particularly attractive advantage of remaining homogeneous and stable when kept in storage at ambient temperature and at temperatures of up to 50° C.

The compositions dispensed from the pressurized aerosol device form gels which are initially nonfoaming and which, under the mechanical action such as being spread on the hair or the skin by hand or by massage, generate an abundant, stable and uniform foam which is essentially uniform from the initial to the final use of the contents of the aerosol device.

The foam produced in this manner is particularly light and soft to the touch, and this constitutes another advantage when compared with the foams which could be produced according to the state of the art. It imparts more sheen and softness to hair and more softness to the skin.

A subject of the invention is therefore a composition pressurized in an aerosol device and intended to be used for the cosmetic treatment of hair or of the skin, in the form of a delayed-foaming gel and containing at least one delayed-foaming agent and a heterobiopolysaccharide.

Another subject of the invention is a process for the cosmetic treatment of hair or of the skin by virtue of a composition of this kind.

Other subjects of the invention will become apparent from reading the description and the examples which follow.

The cosmetic composition according to the invention, intended to be employed for the cosmetic treatment of hair or of the skin is characterized in that it is in the form of a delayed-foaming gel containing, in a cosmetically acceptable aqueous medium, at least one surface agent, at least one heterobiopolysaccharide and at least one delayed-foaming agent said gel forming a foam after being spread on the hair or the skin.

The surface agents present in the compositions are known per se and are chosen from anionic, nonionic, amphoteric or cationic surface agents or a mixture thereof. Their concentration is generally between 0.1 and 50% and preferably between 0.5 and 20% based on the total weight of the composition. As is well known, these agents may have detergent properties, in which case the composition has hair or skin cleansing properties, in addition to the cosmetic treatment properties.

A particularly attractive embodiment consists in the use of at least one cationic surface agent in the composition. These cationic surface agents, which are known per se, are chosen more particularly from the compounds corresponding to the formula:

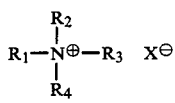  (I)

in which (i) $R_1$ denotes a mixture of alkenyl and/or alkyl radicals containing from 10 to 22 carbon atoms derived from tallow, copra or soya fatty acids or a $C_{12}$ alkyl radical, the groups $R_2$, $R_3$ and $R_4$ denoting a methyl group, (ii) $R_1$ denotes a $C_{16}H_{33}$ group and $R_2$ and $R_3$ denote a $CH_3$ group, $R_4$ denoting a $CH_2—CH_2—OH$ group, or alternatively all three $R_2$, $R_3$ and $R_4$ denote a methyl group, $X^\ominus$ denoting a halide anion and preferably $Cl^\ominus$.

Other cationic surface agents which are preferentially employed in the compositions according to the invention correspond to the formula (II)

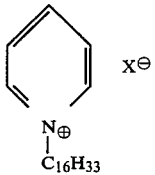  (II)

in which $X^\ominus$ denotes a halide anion and preferably $Cl^\ominus$.

These cationic surface-active agents are present in the compositions according to the invention in proportions which are preferably between 0.1 and 5% and in particular between 0.5 and 3% by weight based on the total weight of the composition.

The heterobiopolysaccharides employed in accordance with the invention are known per se and are produced, in particular, by the fermentation of sugars by microorganisms. These heterobiopolysaccharides generally comprise glucose, mannose and glucuronic or galacturonic acid units in their structure.

Among these heterobiopolysaccharides, those more particularly preferred are the scleroglucanes or the xanthane gums produced by the action of the bacterium *Xanthomonas campestri* and the mutants or variants thereof having a molecular weight of between 1,000,000 and 50,000,000. The xanthane gums have a viscosity of between 0.60 and 1.65 Pa s in the case of an aqueous composition containing 1% of xanthane gum, measured with a Brookfield type LVT viscometer at 60 revolutions/minute. In their structure, they comprise 3 different monosaccharides which are mannose, glucose and glucuronic acid. Products which are particularly preferred are those marketed under the trade name "Keltrol" by the Kelco company, a 1% aqueous solution of which has a Brookfield LVT viscosity of 1.2 to 1.6 Pa s at 60 revolutions/minute, Kelzan S marketed by the Kelco company, a 1% aqueous solution of which has a Brookfield LVT viscosity of 0.850 Pa s at 60 revolutions/minute, Rhodopol 23, 23 U and 23 C, which are marketed by the Rhône-Poulenc company, a 0.3% aqueous solution of which has a Brookfield LVT viscosity of 0.450±0.050 Pa s at 30 revolutions/minute, Rhodigel 23 sold by the Rhône-Poulenc company, Deuteron XG marketed by the Schoener GmbH company, a 1% aqueous solution of which has a viscosity of 1.200 Pa s, measured with a Brookfield LVT viscometer at 30 revolutions/minute, the scleroglucane sold under the trade name "Actigum CX9" by the Ceca company which has a viscosity of 1.200 Pa s, measured with a Brookfield LVT viscometer at 30 revolutions/minute in the case of a 1% aqueous solution or the products sold by the Kelco company under the trade names "Kelzan K3 B130, K8 B12" whose Haake Rotovisco RV1, MV1 viscosity at 25° C. is 1 Pa s at $10s^{-1}$ and K9 C57 whose viscosity of 1% aqueous solution is from 0.63 to 1 Pa s, measured with a Brookfield LVS viscometer at 60 revolutions/minute.

Other heterobiopolysaccharides which may be employed in accordance with the invention may be chosen from:

the biopolymer PS 87 generated by the bacterium *Bacillus polymyxa* which comprises glucose, galactose, mannose, fucose and glucuronic acid in its structure; this biopolymer PS 87 is described more particularly in the published European Patent Application No. 23,397;

the biopolymer S88 generated by the strain Pseudomonas ATCC 31554 which comprises rhamnose, glucose, mannose and glucuronic acid in its structure; this biopolymer is described in British Patent No. 2,058,106;

the biopolymer S130 generated by the strain Alcaligenes ATCC 31555, which comprises rhamnose, glucose, mannose and glucuronic acid in its molecule; this biopolymer is described more particularly in British Patent 2,058,107;

the biopolymer S139 generated by the strain Pseudomonas ATCC 31644 which comprises rhamnose, glucose, mannose, galactose and galacturonic acid in its molecule; this biopolymer is described in particular in U.S. Pat. No. 4,454,316;

the biopolymer S198 generated by the strain Alcaligenes ATCC 31853, which comprises rhamnose, glucose, mannose and glucuronic acid in its molecule; this biopolymer i$ described in particular in European Patent Application 64,354; and the exocellular biopolymer generated by the gram-positive or negative species of bacteria, of yeasts, fungi or algae, which is described in particular in German Patent Application No. 3,224,547.

These heterobiopolysaccharides are employed in the compositions according to the invention in proportions which are preferably between 0.05 and 5% by weight and more particularly between 0.1 and 2% by weight based on the total weight of the composition.

The delayed-foaming agent present in the compositions according to the invention is a $C_{3-6}$ aliphatic hydrocarbon or mixtures thereof. It is chosen more particularly from propane, n-butane, isobutane, isobutylene, n-pentane, isopentane, n-hexane and 2-hexene.

Other delayed-foaming agents are chosen from partially or completely halogenated hydrocarbons such as, more particularly, trichlorotrifluoroethane, 1,2-dichloro-1,1,2,2-tetrafluoroethane or mixtures of these derivatives.

The particularly preferred compositions are those based on $C_3$-$C_6$ hydrocarbons which are mentioned above. These products, which have delayed-foaming properties, generally have a vapour pressure ranging from $0.25 \ 10^5$ to $10^5$ Pa at a temperature of 32°-38° C.

The delayed-foaming agents are used in proportions preferably between 0.5 and 12% by weight and in particular between 1 and 5% by weight based on the total weight of the composition.

A particularly advantageous embodiment of the invention is a composition intended for the cosmetic treatment of hair in the form of a delayed-foaming gel dispensed from an aerosol package with a diaphragm containing, in an aqueous medium, a heterobiopolysaccharide, a cationic surface agent and treatment agents chosen from cosmetically acceptable polymers and the delayed-foaming agent.

The cosmetic polymers which are particularly preferred are cationic and are chosen from polymers containing primary, secondary, tertiary and/or quaternary amine groups forming part of the polymer chain or directly linked to the latter, having a molecular weight of between 500 and approximately 5,000,000.

Among these polymers there may be more particularly mentioned quaternized proteins, quaternized polysiloxanes, and polymers of the polyamine, polyaminoamide and quaternary polyammonium type. These polymers are preferably present in proportions of between 0.25 and 3% by weight based on the total weight of the composition.

The quaternized proteins are, in particular, polypeptides which are chemically modified and which carry quaternary ammonium groups at the end of the chain or grafted onto the latter. Among these proteins there may be mentioned, in particular:

collagen hydrolysates bearing triethylammonium groups such as the products sold under the trade name "Quat-Pro E" by the Maybrook company and called "Triethonium Hydrolyzed Collagen Ethosulfate" in the CTFA dictionary;

collagen hydrolysates bearing trimethylammonium or trimethylstearylammonium chloride groups sold under the trade name of Quat-Pro S by the Maybrook company and called "Steartrimonium Hydrolyzed Collagen" in the CTFA dictionary;

animal protein hydrolysates bearing trimethylbenzylammonium groups such as the products sold under the trade name "Crotein BTA" by the Croda company and called "Benzyltrimonium hydrolyzed animal protein" in the CTFA dictionary; and protein hydrolysates bearing, on the polypeptide chain, quaternary ammonium groups containing at least one alkyl radical containing from 1 to 18 carbon atoms.

Among these protein hydrolysates there may be mentioned, among others:

Croquat L, whose polypeptide chain has a mean molecular weight of approximately 2500 and whose quaternary ammonium group contains a $C_{12}$ alkyl group;

Croquat M, whose polypeptide chain has a mean molecular weight of approximately 2500 and whose quaternary ammonium group contains a $C_{10}$-$C_{18}$ alkyl group;

Croquat S, whose polypeptide chain has a mean molecular weight of approximately 2700 and whose quaternary ammonium group contains a $C_{18}$ alkyl group; and Crotein Q, whose polypeptide chain has a mean molecular weight of the order of 12,000 and whose quaternary ammonium group contains at least one alkyl group containing from 1 to 18 carbon atoms.

These various products are sold by the Croda company.

Other quaternized proteins are those corresponding to the formula:

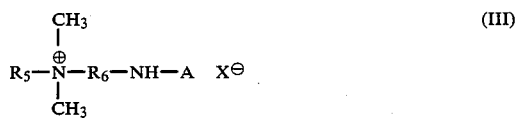

which formula $X^-$ is an anion of an organic or inorganic acid, A denotes a protein residue derived from collagen protein hydrolysates, $R_5$ denotes a lipophile group containing up to 30 carbon atoms, $R_6$ denotes an alkylene group containing 1 to 6 carbon atoms; these proteins have a molecular weight of between 1500 and 10,000, preferably 2000 and 5000. The preferred products are those sold under the trade name "Lexein QX 3000", called "Cocotrimonium Collagen Hydrolyzate" in the CTFA dictionary, by the Inolex company.

Another group of cationic polymers are cationic silicone polymers. Among these polymers there may be mentioned (a) the quaternized polysiloxanes called "Amodimethicone" in the CTFA dictionary and corresponding to the formula:

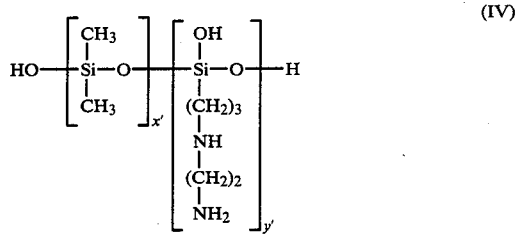

in which x' and y' are integers which depend on the molecular weight which is generally between 5000 and 10,000;

(b) the cationic silicone polymers corresponding to the formula:

in which

G is a hydrogen atom or the phenyl group, OH, a $C_1$-$C_8$ alkyl, and preferably a methyl group, a denotes 0 or an integer from 1 to 3 and preferably 0, b denotes 0 or 1 and preferably 1, the sum (n +m) is an integer from 1 to 2,000 and preferably from 50 to 150, it being possible for n to denote a number from 0 to 1999 and preferably from 49 to 149 and it being possible for m to denote an integer from 1 to 2000 and preferably from 1 to 10;

R' is a monovalent radical of formula $C_qH_{2q}L$ in which q is a number from 2 to 8 and L is chosen from the groups:

$$NR''-CH_2-CH_2-N(R'')_2$$

$$N(R'')_2$$

$$\overset{\oplus}{N}(R'')_3 A^{\ominus}$$

$$\overset{\oplus}{N}(R'')H_2 A^{\ominus}$$

$$NR''CH_2-CH_2-\overset{\oplus}{N}R''H_2 A^{\ominus}$$

which R" may denote hydrogen, phenyl, benzyl, a monovalent saturated hydrocarbon radical and preferably an alkyl radical containing from 1 to 20 carbon atoms and $A^{\ominus}$ denotes a halide ion such a fluoride, chloride, bromide or iodide.

A particularly advantageous product falling within this definition is the polymer called "trimethylsilylamodimethicone" corresponding to the formula:

$$(CH_3)_3-Si-\left[O-\underset{\underset{CH_3}{|}}{\overset{\overset{CH_3}{|}}{Si}}\right]_n-\left[O-\underset{\underset{\underset{\underset{NH_2}{|}}{(CH_2)_2}}{\underset{NH}{|}}}{\overset{\overset{CH_3}{|}}{Si}}\right]_m-OSi(CH_3)_3 \quad (VI)$$

in which n and m have the meanings given above (formula V). Polymers of this kind are described in U.S. patent application 95,238 EP-A;

(c) the cationic silicone polymers corresponding to the formula:

$$(R_7)_3-Si-\left[O-\underset{\underset{R_7}{|}}{\overset{\overset{R_7}{|}}{Si}}-O\right]_r-\left[\underset{\underset{R_7}{|}}{\overset{\overset{R_8-CH_2-CHOH-CH_2-\overset{\oplus}{N}(R_7)_3 Q^{\ominus}}{|}}{Si}}-O\right]_s-Si-(R_7)_3 \quad (VII)$$

in which $R_7$ denotes a monovalent hydrocarbon radical containing from 1 to 18 carbon atoms and in particular an alkyl or alkenyl and preferably methyl radical;

$R_8$ denotes a divalent hydrocarbon radical, preferably a $C_1$-$C_{18}$ alkylene radical or a divalent $C_1$-$C_{18}$ and preferably $C_1$-$C_8$ alkylenoxy radical;

$Q^-$ is a halide ion, preferably chloride;

r denotes a mean statistical value from 2 to 20 and preferably from 2 to 8;

s denotes a mean statistical value from 20 to 200 and preferably from 20 to 50.

Polymers of this kind are described more particularly in U.S. Pat. No. 4,185,087.

A particularly preferred polymer which is a member of this class is the polymer sold by the Union Carbide company under the trade name "Ucar Silicone ALE 56" which is characterized by a flash point of 60° C. according to the ASTM standard D-93, a viscosity of 0.011 Pa s at a concentration of 35% of active substance and at 25° C. and by a total basicity index of 0.24 meq/g.

When these silicone polymers are employed, a particularly advantageous embodiment is their use together with cationic surface agents or nonionic surface agents. In the compositions according to the invention it is possible to use, for example, the commercial product sold under the trade name "Emulsion Cationique DC 929" by the Dow Corning company which contains the amodimethicone of formula (IV), a cationic surface agent corresponding to the formula:

$$R_9-\overset{\overset{CH_3}{|}}{\underset{\underset{CH_3}{|}}{N^{\oplus}}}-CH_3 \quad Cl^{\ominus} \quad (VII)$$

in which $R_9$ denotes a mixture of alkenyl and/or alkyl radicals containing from 14 to 22 carbon atoms derived from tallow fatty acids, and a nonionic surface agent of formula:

$$C_9H_{19}-C_6H_4-(OC_2H_4)_{10}-OH$$

known under the trade name "Nonoxynol 10".

Another composition which may be employed in this embodiment of the invention is the composition containing the product sold under the trade name "Dow Corning Q2 7224" by the Dow Corning company containing a combination of the trimethylsilylamodimethicone of formula (VI), a nonionic surface agent of formula:

$$C_8H_{17}-C_6H_4-(OCH_2CH_2)_n-OH \quad \text{where } n = 40$$

also called octoxynol-40, another nonionic surface agent of formula:

$$C_{12}H_{25}-(OCH_2-CH_2)_n-OH \quad \text{where } n = 6$$

also called isolaureth-6 and glycol.

The polymers of the polyamine, polyaminoamide and quaternary polyammonium type which can be employed in accordance with the present invention are described in particular in the applicant's French Patent Nos. 82/07,996 or 84/04,475. Among these polymers, there may be mentioned:

(1) The vinylpyrrolidone/dialkylaminoalkyl acrylate or methacrylate copolymers, quaternized or otherwise, such as the products sold under the trade name "Gafquat" by the GAF Corporation such as, for example, "Gafquat 734 or 755" or the product called "Copolymer 845". These polymers are described in detail in French Patent Nos. 2,077,143 and 2,393,573.

(2) The cellulose ether derivatives containing quaternary ammonium groups described in French Patent No. 1,492,597 and in particular the polymers marketed under the trade names "JR" (JR 400, JR 125, JR 30M) or "LR" (LR 400, LR 30M) by the Union Carbide Corporation. The polymers are also defined in the CTFA dictionary as hydroxyethylcellulose quaternary ammoniums which have reacted with an epoxide substituted by a trimethylammonium group.

(3) Cationic cellulose derivatives such as cellulose copolymers or cellulose derivatives grafted with a water-soluble quaternary ammonium monomer and described in greater detail in U.S. Pat. No. 4,131,576, such as hydroxyalkylcelluloses such as hydroxymethyl, hydroxyethyl or hydroxypropyl cellulose grafted with a methacryloylethyltrimethylammonium, methacrylamidopropyltrimethylammonium or dimethyldiallylammonium salt.

The commercial products corresponding to this definition are more particularly the products sold under the trade name "Celquat L 200" and "Celquat H 100" by the National Starch company.

(4) The cationic polysaccharides described more particularly in U.S. Pat. Nos. 3,589,578 and 4,031,307 and more particularly the product marketed under the trade name "Jaguar C. 13 S" sold by the Meyhall company.

(5) Polymers consisting of piperazinyl repeat units and of divalent alkylene or hydroxyalkylene radicals containing straight or branched chains interrupted, if desired, by oxygen, sulphur or nitrogen atoms or by aromatic or heterocyclic rings, as well as the oxidation and/or quaternization products of these polymers. Polymers of this kind are described in French Patent Nos. 2,162,025 and 2,280,361.

(6) The water-soluble polyaminopolyamides prepared in particular by polycondensation of an acidic compound with a polyamine. These polyaminoamides may be crosslinked with an epihalohydrin, a diepoxide, a dianhydride, an unsaturated anhydride, a bis-unsaturated derivative, a bishalohydrin, a bisazetidinium, a bishaloacyldiamine, an alkyl bishalide or with an oligomer resulting from the reaction of a difunctional compound reactive towards a bishalohydrin, a bisazetidinium, a bishaloacyldiamine, an alkyl bishalide, an epihalohydrin, a diepoxide or a bisunsaturated derivative; the crosslinking agent being used in proportions ranging from 0.025 to 0.35 mole per amino group of the polyaminopolyamide.

These polyaminopolyamides may be alkylated or, if they contain one or more tertiary amine groups, quaternized. Such polymers are described in particular in French Patent Nos. 2,252,840 and 2,368,508.

(7) The polyaminopolyamide derivatives resulting from the condensation of polyalkylenepolyamines with polycarboxylic acids, followed by an alkylation with difunctional agents. There may be mentioned, for example, the adipic acid/dialkylaminohydroxyalkyl/dialkylenetriamine polymers in which the alkyl radical contains from 1 to 4 carbon atoms and preferably denotes methyl, ethyl and propyl. Such polymers are described in French Patent No. 1,583,363.

Among these derivatives there may be more particularly mentioned the adipic acid/dimethylaminohydroxypropyl/diethylenetriamine polymers sold under the trade names "Cartaretine F, F₄ or F₈" by the Sandoz company.

(8) The polymers obtained by the reaction of a polyalkylenepolyamine containing two primary amine groups and at least one secondary amine group with a dicarboxylic acid chosen from diglycolic acid and saturated aliphatic dicarboxylic acids containing from 3 to 8 carbon atoms; the molar ratio between the polyalkylenepolyamine and the dicarboxylic acid being between 0.8:1 and 1.4:1; the polyaminopolyamide resulting therefrom being made to react with the epichlorohydrin in a molar ratio of epichlorohydrin in relation to the secondary amine group of the polyaminopolyamide of between 0.5:1 and 1.8:1. Such polymers are described in particular in U.S. Pat. Nos. 3,227,615 and 2,961,347.

Polymers of this type are, in particular, marketed under the trade name "Hercosett 57" by the Hercules Incorporated company and these polymers have a viscosity of 0.03 Pa s as a 10% aqueous solution at 25° C., or alternatively under the trade name of "PD 170" or "Delsette 101" by the Hercules company in the case of the adipic acid/epoxypropyl/diethylenetriamine copolymer.

(9) Cyclopolymers having a molecular weight of 20,000 to 3,000,000 such as homopolymers comprising as a main chain constituent repeat units corresponding to the formulae (IX) or (IX')

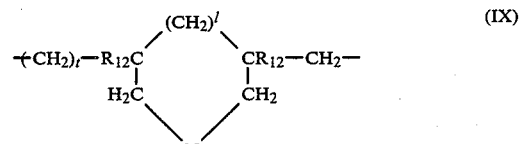

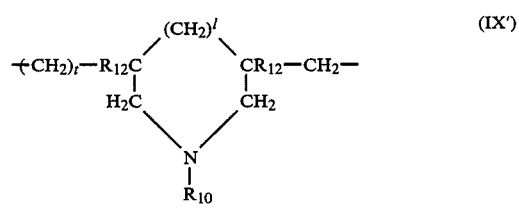

l and t are equal to 0 or 1, and the sum l+t=1, $R_{12}$ denotes hydrogen or methyl, $R_{10}$ and $R_{11}$ independently of each other denote an alkyl group containing from 1 to 22 carbon atoms, a hydroxyalkyl group in which the alkyl group has preferably 1 to 5 carbon atoms, a lower amidoalkyl group and where $R_{10}$ and $R_{11}$ may denote, together with the nitrogen atom to which they are attached, heterocyclic groups such as piperidyl or morpholinyl, as well as copolymers containing the units of formula (IX) or (IX') and units of acrylamide or of diacetoneacrylamide derivatives, and $Y^{\ominus}$ is an anion such as bromide, chloride, acetate, borate, citrate, tartrate, bisulphate, bisulphite, sulphate or phosphate. Among the polymers defined above there may be mentioned more particularly the dimethyldiallylammonium chloride homopolymer sold under the trade name Merquat 100 having a molecular weight of less than 100,000 and the copolymer of dimethyldiallylammonium chloride with acrylamide having a molecular weight greater than 500,000 and sold under the trade name of Merquat 550 by the Merck company.

These polymers are described more particularly in French Patent No. 2,080,759 and its Certificate of Addition No. 2,190,406.

(10) The quaternary polyammonium polymer containing repeat units corresponding to the formula:

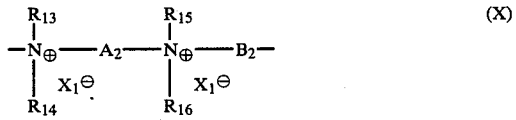

in which $R_{13}$ and $R_{14}$, $R_{15}$ and $R_{16}$ being identical or different, denote aliphatic, alicyclic or arylaliphatic radicals containing from 1 to 20 carbon atoms or lower hydroxyalkylaliphatic radicals, or alternatively $R_{13}$ and $R_{14}$ and $R_{15}$ and $R_{16}$ together or separately form, with the nitrogen atoms to which they are attached, heterocyclic rings optionally containing a second heteroatom other than nitrogen or alternatively $R_{13}$, $R_{14}$, $R_{15}$ and $R_{16}$ denote a linear or branched $C_2$-$C_6$ alkyl radical substituted by a nitrile, ester, acyl, amide or

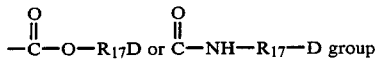

group where $R_{17}$ is an alkylene and D a quaternary ammonium group.

$A_2$ and $B_2$ denote polymethylenic groups containing from 2 to 20 carbon atoms which may be linear or branched, saturated or unsaturated and which may contain, linked to or inserted into the main chain, one or more aromatic rings or one or more oxygen or sulphur atoms or SO, $SO_2$, disulphide, amino, alkylamino, hydroxyl, quaternary ammonium, ureido, amide or ester groups and $X^{\ominus}_1$ denotes an anion derived from an inorganic or organic acid.

$A_2$ and $R_{13}$ and $R_{15}$ may form a piperazine ring with the two nitrogen atoms to which they are attached; furthermore, when $A_2$ denotes a linear or branched, saturated or unsaturated alkylene or hydroxyalkylene radical, $B_2$ may also denote a group:

$$-(CH_2)_n-CO-D-OC-(CH_2)_n-$$

in which D denotes:

(a) a glycol residue of formula: O—Z—O— where Z denotes a linear or branched hydrocarbon radical or a group corresponding to the formulae:

$$\dagger CH_2-CH_2-O\dagger_x CH_2-CH_2- \quad (V)$$

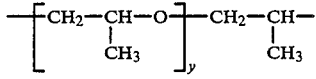

where x and y denote an integer from 1 to 4 representing a specified and unique degree of polymerization or any number from 1 to 4 representing an average degree of polymerization;

(b) a bis-secondary diamine residue such as a piperazine derivative, (c) a bis-primary diamine residue of formula:

$$-NH-Y-NH-$$

where Y denotes a linear or branched hydrocarbon radical or alternatively the divalent radical $$-CH_2-CH_2-S-S-CH_2-CH_2-$$

(d) a ureylene group of formula:

$$-NH-CO-NH-;$$

$X^{\ominus}$ is an anion such as chloride or bromide.

These polymers have a molecular mass which is generally between 1,000 and 100,000.

Polymers of this type are described in particular in French Patent Nos. 2,320,330, 2,270,846, 2,316,271, 2,336,434 and 2,413,907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

(11) The quaternary polyammonium polymers consisting of repeat units of formula:

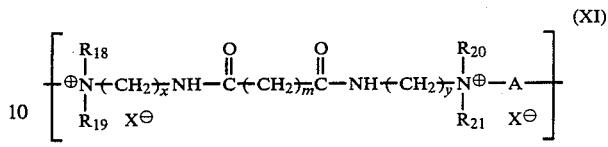

in which $R_{18}$, $R_{19}$, $R_{20}$ and $R_{21}$, which are identical or different, denote a hydrogen atom or a methyl, ethyl, propyl, $\beta$-hydroxyethyl, $\beta$-hydroxypropyl or $-CH_2CH_2(OCH_2CH_2)_pOH$ radical where p is equal to 0 or an integer from 1 to 6, provided that $R_{18}$, $R_{19}$, $R_{20}$ and $R_{21}$ do not simultaneously denote a hydrogen atom, x and y, identical or different, are integers from 1 to 6;

m is equal to 0 or an integer from 1 to 34,

X denotes a halogen atom,

A denotes the residue of a dihalide radical and preferably denotes $$-CH_2-CH_2-O-CH_2-CH_2-$$

Such compounds are described in further detail in European Patent Application No. 122,324.

(12) Homopolymers or copolymers derived from acrylic or methacrylic acids and comprising, as repeat unit:

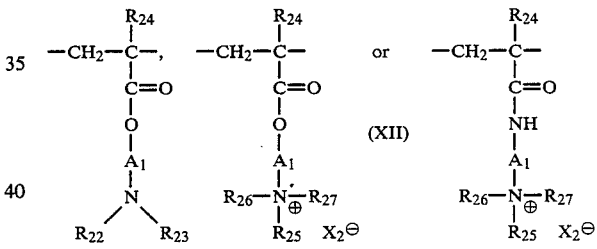

in which $R_{24}$ denotes H or $CH_3$, $A_1$ is a linear or branched alkyl group containing from 1 to 6 carbon atoms or a hydroxyalkyl group containing from 1 to 4 carbon atoms, $R_{25}$, $R_{26}$ and $R_{27}$, which are identical or different, denote an alkyl group containing from 1 to 18 carbon atoms or a benzyl radical, $R_{22}$ and $R_{23}$ denote hydrogen or an alkyl group containing from 1 to 6 carbon atoms, and $X_2^-$ denotes a methosulphate or a halide anion such as chloride or bromide.

The comonomer or the comonomers which may be employed belong to the group of: acrylamide, methacrylamide, diacetoneacrylamide, acrylamide and methacrylamide which are substituted by lower alkyls on the nitrogen, alkyl esters of acrylic or methacrylic acids, vinylpyrrolidone and vinyl esters.

(13) Quaternary vinylpyrrolidone and vinylimidazole polymers such as, for example, the products marketed under the trade names Luviquat FC 905, FC 550 and FC 370 by the BASF Company.

Other cationic polymers which may be employed in accordance with the invention are polyalkyleneimines, especially polyethyleneimines, polymers containing vinylpyridine or vinylpyridinium repeat units, condensates of polyamines with epichlorohydrin, quaternary polyureylenes and chitin derivatives.

The polymers which are particularly preferred in the compositions in accordance with the invention are the polymers corresponding to the formulae:

the polymer comprising the repeat units of formula:

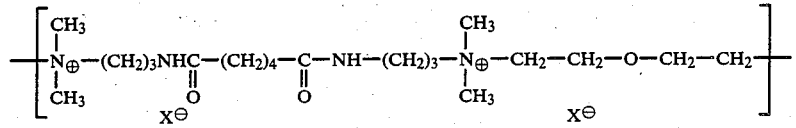

sold under the trade name "Mirapol AD 1" by the Miranol company, the polymer comprising the repeat units of formula:

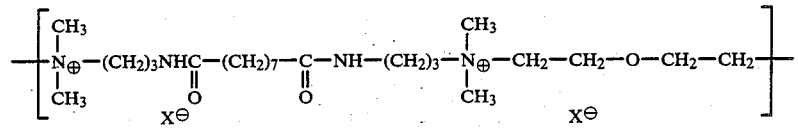

sold under the trade name "Mirapol AZ 1" by the Miranol company, the poly(methacrylamidopropyltrimethylammonium chloride) sold under the trade name "Polymaptac" by the Texaco Chemicals company;

a quaternized polymer of the ionene type described in the Applicant's French Patent No. 2,270,846 and more particularly those comprising the repeat units:

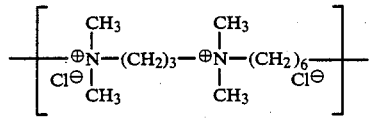

the dimethyldiallylammonium cyclopolymers sold under the trade names "merquat 100" and "Merquat 550" by the Merck company;

quaternary vinylpyrrolidone and vinylimidazole polymers such as those sold under the trade names "Luviquat FC 905, FC 550 and FC 370" by the BASF company;

quaternized or unquaternized vinylpyrrolidone/-dialkylaminoalkyl acrylate or methacrylate copolymers such as the products sold under the trade names "Copolymer 845", "Gafquat 734 or 755" by the GAF company;

quaternary cellulose ether polymers such as those sold under the trade names "JR" such as for example JR 125, JR 400, JR 30M and LR such as LR 400 and LR 30 by the Union Carbide Corporation;

cationic cellulose derivatives such as the products sold under the trade names "Celquat L 200" and "Celquat H 100" by the National Starch company;

quaternary ammonium polymers of the type described in U.S. Pat. No. 4,157,388 and more particularly the polymer comprising repeat units of formula:

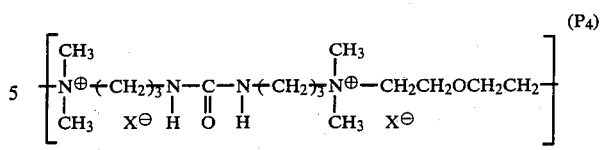

sold under the trade name of "Mirapol A 15" by the Miranol company;

the poly(dimethylbutenylammonium chloride)-α,ω-bis(triethanolammonium chloride) sold more particularly under the trade name of "Onamer M" by the Onyx Internationale company.

The compositions in accordance with the invention may optionally contain an electrolyte chosen from alkali metal salts such as the sodium, potassium or lithium salts of halides such as chloride or bromide or of sulphate or of organic acids such as acetates or lactates, as well as from alkaline-earth metal salts such as calcium, magnesium or strontium carbonates, silicates, nitrates, acetates, gluconates, pantothenates or lactates. When present, these electrolytes are preferably employed in proportions of between 0.25 and 8% by weight based on the total weight of the composition and especially between 1 and 4% by weight.

The compositions in the form of delayed-foaming aqueous gels in accordance with the invention may be employed as a shampoo, a rinsing product to be applied before or after shampooing, before or after dyeing or bleaching, before or after permanent waving or hair-straightening, as shaving gels, shower gels, as products not intended to be rinsed such as hairdressing, conditioning or hair-setting gels.

In the event of their use for the skin, especially in the form of shaving gels, in addition to the above-mentioned constituents they contain a water-soluble soap such as a water-soluble salt of $C_{12}$–$C_{18}$ fatty acids which is well known in the state of the art. Such soaps are present in a proportion of 4 to 25% by weight based on the total weight of the composition.

When the compositions in accordance with the invention are intended to be employed as rinsed products for the hair or the skin, a particularly preferred form consists of the compositions containing a cationic surface agent as defined above in the presence of electrolyte, optionally of one or more cationic cosmetic polymers as defined above. Their pH is generally between 3 and 9 and preferably between 4 and 8.

A preferred delayed-foaming gel of the invention which can be employed for rinsing hair contains:

(a) a heterobiopolysaccharide chosen from xanthane gums (b) a $C_3$–$C_6$ aliphatic hydrocarbon and preferably a $C_5$ aliphatic hydrocarbon such as isopentane or pentane, (c) an electrolyte (d) a cationic surface agent corresponding to the formula:

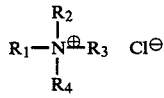

in which $R_1$ denotes a mixture of alkenyl and/or alkyl radicals containing from 14 to 22 carbon atoms derived from tallow fatty acids with $R_2$, $R_3$ and $R_4$, identical, denoting $CH_3$; or alternatively $R_1$ denotes $C_{16}H_{33}$ and $R_2$, $R_3$, identical, denote methyl and $R_4$ denotes $CH_2CH_2OH$ or yet again $R_1$ denotes $C_{16}H_{33}$ and $R_2$, $R_3$ and $R_4$, identical, denote methyl and (e) at least one cationic polymer chosen from quaternized polysiloxanes, quaternized proteins and quaternary polyammonium derivatives mentioned under paragraphs (1), (2), (3), (9), (10) and 13 or of formulae $P_1$, $P_2$ and $P_4$ or again poly(methyacrylamidopropyltrimethylammonium chloride) or poly(dimethylbutenylammonium chloride)-$\alpha,\omega$-bis(triethanolammonium chloride).

The delayed-foaming compositions in accordance with the invention may obviously contain any other ingredient which is usually employed in cosmetics, such as perfumes, colorants, preserving agents, sequestering agents, softening agents, sunscreens and treatment agents such as antidandruff agents.

These compositions are packaged in pressurized aerosol devices containing, in addition to the composition in accordance with the invention, propellant agents which may consist of a condensable gas such as a hydrocarbon such as propane, butane, isobutane, isopentane and halogenated hydrocarbons.

Examples of halogenated hydrocarbons which may be employed are more particularly monochlorotrifluoromethane, trichloromonofluoromethane, dichlorodifluoromethane, dichloromonofluoromethane, monochlorodifluoroethane, trichlorotrifluoroethane, dichlorotetrafluoroethane, difluorothane and difluoromonochloroethane, which are more particularly marketed under the trade names "Freon" and "Genetron".

It is also possible to employ mixtures of these propellant agents, especially with noncondensable gases such as nitrous oxide or nitrogen.

These propellant agents are employed in particular in accordance with the invention in jacketed devices in an aerosol package containing a diaphragm, which means that the propellant is separated from the composition. In this form of embodiment, the composition in accordance with the invention containing the delayed-foaming agent is introduced into the middle part of the jacketed aerosol, and the propellant is introduced into the outer jacket which is separated by a compressible plastic membrane from the central part. The aerosol cans are generally filled with the composition in the central part, are crimped with a valve and are then pressurized by introducing the propellent mixture, which fills the outer jacket, through the bottom opening.

Other propellants which may be employed may consist of gases which are noncondensable and are preferably insoluble in the pressurized composition such as nitrogen, argon, neon, krypton, xenon, helium, radon, nitrous oxide and carbon dioxide. This type of noncondensable propellant is introduced into the upper part of an aerosol package fitted with a dip tube. In this case, the propellant which is noncondensable and insoluble in the composition containing the active substances acts as a piston and expels the composition through the dip tube.

The hair or skin treatment process consists in applying the nonfoaming gel expelled from the pressurized aerosol device and in forming a foam by spreading by hand or by any other means such as a shaving brush in the case of shaving gels.

The following examples are intended to illustrate the invention without, however, being of a limiting nature.

EXAMPLE 1

A self-foaming after-shampoo having the following composition is produced:

| | |
|---|---|
| Heterobiopolysaccharide sold under the trade name "Actigum CX9" by the Ceca company | 1.2 g |
| Sodium chloride | 4 g |
| Cationic silicone polymer sold under the trade name "Ucar Silicone ALE 56" by the Union Carbide company at the concentration of 35% AS | 1.5 g AS |
| Quaternized protein sold under the trade name Lexein QX 3000 by the Inolex company at the concentration of 30% AS | 1 g AS |
| N—Cetylpyridinium chloride | 0.5 g |
| Preservative, colorant | 100 g |
| HCl, q.s., pH 6 | |
| Water, q.s. | |

95 g of this composition are introduced into the central part of a jacketed aerosol whose inner wall consists of an impervious compressible plastic membrane separating the propellant (outer jacket) from the self-foaming gelled composition (central part).

5 g of pentane are then introduced into the central part. After crimping the valve and slight shaking, the aerosol can is pressurized by introducing a Freon 12/14 propellants mixture (53–47% by weight) which fills the jacket, through the bottom opening.

EXAMPLE 2

A self-foaming after-shampoo having the following composition is prepared:

| | |
|---|---|
| Heterobiopolysaccharide sold under the trade name "Rhodopol" 23 U by the Rhône-Poulenc company | 0.5 g |
| Sodium chloride | 4 g |
| Composition containing a cationic silicone polymer sold under the trade name "Emulsion cationique DC 929" by the Dow Corning company at the concentration of 35% AS | 0.6 g AS of polymer |
| Cationic cellulose derivative sold under the trade name "Celquat L 200" by the National Starch company | 2 g |
| Cetyltrimethylammonium chloride sold under the trade name "Dehyquart A" by the Henkel company at the concentration of 25% AS | 1.5 g AS |
| Preservative, colorant | 100 g |
| Triethanolamine, q.s., pH: 8.5 | |

| | |
|---|---|
| Water, q.s. | |

As in Example 1, 95 g of this composition are introduced into an aerosol can followed by 5 g of pentane. After crimping and shaking the can is pressurized by introducing the Freon propellants mixture through the bottom of the jacket.

EXAMPLE 3

A self-foaming after-shampoo having the following composition is produced:

| | |
|---|---|
| Heterobiopolysaccharide sold under the trade name "Keltrol" by the Kelco company | 2 g |
| Sodium chloride | 2 g |
| Composition containing a cationic silicone polymer sold under the trade name "Dow Corning Q₂ 7224" by the Dow Corning company at the concentration of 35% AS | 2 g AS of polymer |
| Epichlorohydrin condensate with the condensate of adipic acid with diethylenetriamine, prepared according to Example Ia of French Patent 2,252,840 | 0.5 g AS |
| N—Cetylpyridinium chloride | 1 g |
| Preservative, colorant | 100 g |
| Lactic acid, q.s., pH: 4.3 | |
| Water, q.s. | |

As in Example 1, 95 g of this composition are introduced into an aerosol can, followed by 5 g of pentane. After crimping and shaking, the can is pressurized by introducing the Freon propellants mixture through the bottom of the jacket.

EXAMPLE 4

A self-foaming after-shampoo having the following composition is produced:

| | |
|---|---|
| Heterobiopolysaccharide sold under the trade name "Rhodopol 23U" by the Rhône-Poulenc company | 1 g |
| Sodium chloride | 3 g |
| Composition containing a cationic silicone polymer sold under the trade name "Emulsion cationique DC 929" by the Dow Corning company at the concentration of 35% AS | 1 g AS of polymer |
| Quaternized protein sold under the trade name "Lexein QX 3000" by the Inolex company at the concentration of 30% AS | 0.5 g AS |
| Cationic surfactant corresponding to the formula: $$R-\overset{CH_3}{\underset{CH_3}{N^{\oplus}}}-CH_3, Cl^{\ominus}$$ R denoting a mixture of alkenyl and/or alkyl radicals derived from tallow fatty acids and containing from 14 to 22 carbon atoms, sold under the trade name "Arquad T 50" by the AKZO-Chemie company, at the concentration of 50% AS | 0.2 g AS |

| | |
|---|---|
| Preservative, colorant | 100 g |
| NaOH, q.s., pH: 7.5 | |
| Water, q.s. | |

As in Example 1, 95 g of this composition are introduced into an aerosol can followed by 5 g of pentane. After crimping and shaking the can is pressurized by introducing the Freon propellant mixture through the bottom of the jacket.

EXAMPLE 5

A self-foaming shower gel having the following composition is prepared:

| | |
|---|---|
| Heterobiopolysaccharide sold under the trade name of "Rhodopol 23U" by the Rhône-Poulenc company | 0.8 g |
| Sodium chloride | 2 g |
| Cetyltrimethylammonium chloride sold under the trade name "Dehyquart A" by the Henkel company at the concentration of 25% AS | 0.2 g AS |
| Sodium salt of trideceth-7 carboxylic acid of formula: $CH_3-(CH_2)_{11}-CH_2-(OCH_2-CH_2)_6-OCH_2COONa$ sold under the trade name of "Sandopan DTC" by the Sandoz company at the concentration of 68% AS | 10 g AS |
| Preservative, colorants | 100 g |
| HCl, q.s., pH: 7.4 | |
| Water, q.s. | |

As in Example 1, 95 g of this composition are introduced into an aerosol can, followed by 5 g of pentane. After crimping and shaking, the can is pressurized by introducing the Freon propellant mixture through the bottom of the jacket.

EXAMPLE 6

A self-foaming shampoo having the following composition is prepared:

| | |
|---|---|
| Heterobiopolysaccharide sold under the trade name "Keltrol" by the Kelco company | 3 g |
| N—Cetylpyridinium chloride | 0.1 g |
| Glucoside alkyl ether sold under the trade name of "Triton" CG 110 by the Seppic company at the concentration of 60% AS | 15 g AS |
| Preservative, colorant, perfume | 100 g |
| Citric acid, q.s., pH: 5 | |
| Water, q.s. | |

As in Example 1, 95 g of this composition are introduced into an aerosol can, followed by 5 g of pentane. After crimping and shaking, the can is pressurized by introducing the Freon propellants mixture through the bottom of the jacket.

EXAMPLE 7

An antidandruff gel of the following composition is prepared:

| | |
|---|---|
| N—Cetylpyridine chloride | 3 g |
| Xanthane gum sold under the trade name of "Rhodopol 23U" by the Rhône-Poulenc company | 1.2 g |

-continued

| | |
|---|---|
| Quaternized hydroxyethyl cellulose sold under the trade name "JR 400" by the Union Carbide company | 0.3 g |
| Sodium chloride | 4 g |
| 1-Hydroxypyridine-2-thione zinc salt sold under the trade name "Omedine de zinc" containing 50% AS by the Olin company | 0.5 g AS |
| Triethanolamine, q.s., pH: 8 | |
| Water, q.s. | 100 g |

As in Example 1, 92.5 g of this composition are introduced into an aerosol can, followed by 7.5 g of isopentane.

After crimping and shaking, the can is pressurized by introducing the Freon propellant mixture through the bottom of the jacket.

The term "lower" used in the specification means a group containing preferably 1 to 4 carbon atoms.

We claim:

1. A cosmetic composition suitable for the treatment of the hair or of the skin in the form of a delayed-foaming gel, which consists essentially of one surface-active agent, one heterobiopolysaccharide and one delayed-foaming agent which is able to form a foam after the composition is spread on the hair or the skin, in a cosmetically acceptable medium.

2. A composition according to claim 1 wherein the surface-active agent is present in an amount of from 0.1 to 50% by weight, the heterobiopolysaccharide is present in an amount of from 0.05 to 5% by weight and the delayed-foaming agent is present in an amount of from 0.5 to 12% by weight, all the above amounts being relative to the total weight of the composition.

3. A composition according to claim 1 wherein the heterobiopolysaccharide is soluble in water and comprises at least glucose, mannose and glucuronic or galacturonic acid units in its structure.

4. A composition according to claim 3 wherein the heterobiopolysaccharide is a xanthane gum having a molecular weight of from 1,000,000 to 50,000,000 or biopolymer PS87 which comprises glucose, galactose, mannose, fructose and glucuronic acid units in its structure produced by Bacillus polymyxa, biopolymer S88 produced by the AZTCC 31554 strain of Pseudomonas, biopolymer S130 produced by the strain Alcaligenes ATCC 31555, biopolymer S 198 comprising rhamnose, glucose, mannose, and glucuronic acid units in its structure produced by the strain Alcaligenes ATCC 31853, biopolymer S 139 comprising rhamnose, glucose, mannose, galactose and galacturonic acid units in its structure produced by the strain Pseudomonas ATCC 31644 or an exocellular biopolymer produced by the gram-positive or negative species of bacteria, yeast or fungi.

5. A composition according to claim 1 wherein the delayed-foaming agent is at least one $C_3$–$C_6$ aliphatic hydrocarbon.

6. A composition according to claim 5 wherein the delayed-foaming agent is propane, n-butane, isobutane, isobutylene, n-pentane, isopentane, n-hexane or 2-hexene.

7. A composition according to claim 1 wherein the delayed-foaming agent is a completely or partially halogenated hydrocarbon.

8. A composition according to claim 1 wherein the delayed-foaming agent has a vapour pressure of $0.25 \times 10^5$ to $10^5$ Pa s at a temperature of 32°–38° C.

9. A composition according to claim 1 which additionally comprises an electrolyte in an amount of from 0.25 to 8% by weight relative to the total weight of the composition.

10. A composition according to claim 1 in the form of a shampoo wherein at least one of the surface-active agents present therein has detergent properties.

11. A composition according to claim 1 in the form of a rinsing product intended to be applied before or after shampooing, before or after dyeing or bleaching, before or after permanent waving or hair-straightening, as a hairdressing, conditioning or hair-setting gel.

12. A composition according to claim 1 in the form of a shaving gel which additionally comprises at least one water-soluble soap in an amount of from 4 to 25% by weight relative to the total weight of the composition.

13. A composition according to claim 1 which comprises, in an aqueous medium:
(a) a xanthane gun,
(b) a $C_3$–$C_6$ aliphatic hydrocarbon,
(c) an electrolyte,
(d) a cationic surface-active agent product of formula

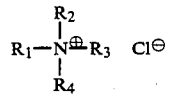

in which $R_1$ is a mixture of alkenyl and/or alkyl groups containing from 14 to 22 carbon atoms derived from tallow fatty acids, $R_2$, $R_3$ and $R_4$ are all methyl groups, or $R_1$ is a $C_{16}H_{33}$ group, $R_2$ and $R_3$ are both methyl groups and $R_4$ is a $Ch_2CH_2OH$ group or a methyl group, and (e) a quaternized polysiloxane, quaternized protein or quaternary polyammonium polymer as defined in paragraphs (1), (2), (3), (9), (10) or (13) in claim 17 or as defined in claim 18 or a polymer comprising units of formula:

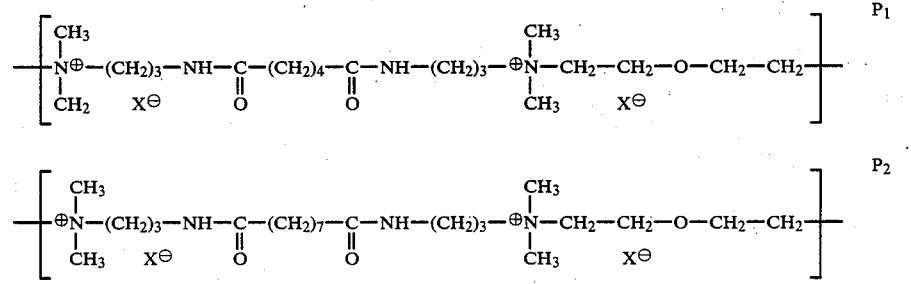

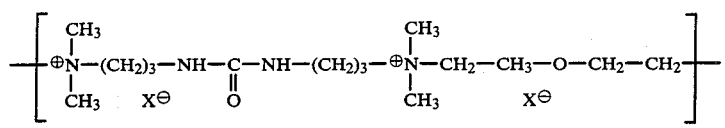

P4 in which X is a halogen,
or poly(dimethylbutenylammonium chloride), -bis(-triethanolammonium chloride) or poly(methacrylamidopropyltrimethylammonium chloride).

14. A composition according to claim 1 which comprises, in a cosmetically acceptable aqueous medium,
(a) a cationic surface-active agent product of formula:

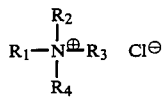

in which R is a mixture of alkenyl and/or alkyl groups containing from 14 to 22 carbon atoms derived from tallow fatty acids and $R_2$, $R_3$ and $R_4$ are all methyl groups or $R_1$ is a $C_{16}H_{33}$ group and $R_2$ and $R_3$ are both methyl groups and $R_4$ is a $CH_2CH_2OH$ group or a methyl group;
(b) a xanthane gum,
(c) pentane or isopentane, and
(d) a quaternary polysiloxane or quaternary protein having a molecular weight of from 1,500 to 10,000 of formula (III):

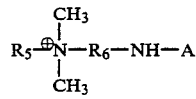   (III)

in which A is a protein residue derived from collagen protein hydrolysate, $R_5$ is a lipophile group containing up to 30 carbon atoms and $R_6$ is an alkylene group containing from 1 to 6 carbon atoms.

15. A composition according to claim 1 which additionally comprises a perfume, colorant, preserving agent, sequestering agent, softening agent or sunscreen.

16. A cosmetic hair or skin treatment which comprises applying at least one composition as defined in claim 1 to the skin or the hair in the form of a nonfoaming gel from an aerosol device and forming a foam on the hair or the skin by the mechanical action of spreading.

17. A cosmetic composition suitable for the treatment of the hair or the skin in the form of a delayed-forming gel, which consists essentially of one cationic surface-active agent, one heterobiopolysaccharide, and one delayed-foaming agent in a cosmetically acceptable medium.

18. A composition according to claim 17 wherein the cationic surface-active agent is either a product of formula:

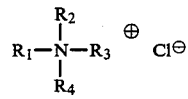   (I)

in which
$R_1$ is a mixture of alkenyl and/or alkyl groups containing from 10 to 22 carbon atoms derived from tallow, copra or soya fatty acids or a $C_{12}$ alkyl group and $R_2$, $R_3$ and $R_4$ are identical and are methyl groups or alternatively $R_1$ is a $C_{16}H_{33}$ group, and $R_2$ and $R_3$ are methyl groups and $R_4$ is a $-CH_2-CH_2-OH$ group or a methyl group;
or a compound of formula:

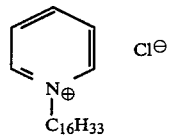   (II)

19. A composition suitable for the treatment of the hair or the skin, in the form of a delayed-foaming gel, which consists essentially of one surface-active agent, one heteropolysaccharide, one delayed-foaming agent in a cosmetically acceptable medium, and one cosmetically useful cationic polymer containing primary, secondary, tertiary and/or quaternary amine groups, having a molecular weight of from 500 to 5,000,000, in a cosmetically acceptable medium. pg,46

20. A composition according to claim 19 wherein the cationic polymer is a quaternized protein comprising a polypeptide which is chemically modified to carry at least one quaternary ammonium group at the end of the chain or grafted onto the chain.

21. A composition according to claim 20 wherein the quaternized protein is a collagen hydrolysate bearing triethylammonium groups, a collagen hydrolysate bearing trimethylammonium or trimethylstearylammonium chloride groups, a protein hydrolysate bearing trimethylbenzylammonium groups, a protein hydrolysate bearing, on the polypeptide chain, quaternary ammonium groups containing at least one alkyl group containing from 1 to 18 carbon atoms, a quaternized protein having a molecular weight of from 1500 to 10,000 of formula:

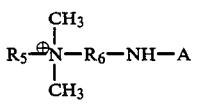   (III)

in which A is a protein residue derived from collagen protein hydrolysate, $R_5$ is a lipophile group containing up to 30 carbon atoms, and $R_6$ is an alkylene group containing from 1 to 6 carbon atoms.

22. A composition according to claim 19 wherein the cationic polymer is a cationic silicone polymer.

23. A composition according to claim 22 wherein the cationic silicone polymer is:
a polymer of formula:

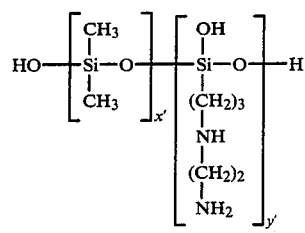

in which x' and y' are each integers such that the molecular weight of the polymer is from 5000 to 10,000,
a polymer of formula:

in which G is hydrogen, a phenyl group, a hydroxy group or a C$_1$–C$_8$ alkyl group; a is from 0 to 3; b is from 0 to 1; n +m is from 1 to 2000; n is from 0 to 1999, m is from 1 to 2000 and R' is a monovalent group of formula:

$C_qH_{2q}L$ in which q is an integer from 2 to 8 and L is a group chosen from:

NR''—CH$_2$—CH$_2$—N(R'')$_2$

N(R'')$_2$

$\overset{\oplus}{N}(R'')_3 A^{\ominus}$

$\overset{\oplus}{N}(R''—H_2)A^{\ominus}$

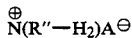
NR''CH$_2$—CH$_2$—$\overset{\oplus}{N}$R''H$_2$A$^{\ominus}$ in which R' is hydrogen, a phenyl group, a benzyl group or a monovalent saturated hydrocarbon group containing from 1 to 20 carbon atoms and A is a halogen; or
a polymer of formula:

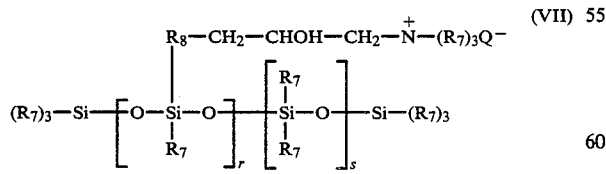

in which R$_7$ is a monovalent hydrocarbon group containing from 1 to 18 carbon atoms, R$_8$ is a divalent hydrocarbon group or a divalent C$_1$–C$_{18}$ alkyleneoxy group, Q$^-$ is a halide anion, r is a mean statistical value from 2 to 20, and s is a mean statistical value from 20 to 200, all the above polymers either being block copolymers or random copolymers.

24. A composition according to claim 19 wherein the cationic polymer is:
(1) a quaternized or unquaternized vinylpyrrolidone/dialkylaminoalkyl acrylate or methacrylate copolymer;
(2) a cellulose ether derivative comprising quaternary ammonium groups;
(b 3) a cellulose or cellulose derivative copolymer grafted with a water-soluble quaternary ammonium monomer;
(4) a cationic polysaccharide;
(5) a polymer comprising piperazinyl repeat units and divalent alkylene or hydroxyalkylene groups with straight or branched chains optionally interrupted by oxygen, sulphur or nitrogen or by aromatic or heterocyclic rings, or an oxidation and/or quaternization product of these polymers;
(6) a water-soluble polyaminopolyamide which is a polycondensate of an acidic compound with a polyamine, optionally crosslinked with an epihalohydrin, a diepoxide, a dianhydride, an unsaturated anhydride, a bis-unsaturated derivative, a bishalohydrin, a bisazetidinium, a bishaloacyldiamine or an alkyl bishalide or again with an oligomer resulting from the reaction of a difunctional compound reactive towards a bishalohydrin, a bisazetidinium, a bishaloacyldiamine, an alkyl bishalide, an epihalohydrin, a diepoxide or a bis-unsaturated derivative, the crosslinking agent being employed in an amount of from 0.025 to 0.35 mole per amine group of the polyaminopolyamine, or an alkylated or quaternized derivative thereof;
(7) a polyaminopolyamide derivative produced from the condensation of a polyalkylenepolyamine with a polycarboxylic acid followed by an alkylation using a difunctional agent;
(8) a product of the reaction of a polyalkylenepolyamine containing two primary amine groups and at least one secondary amine group with a dicarboxylic acid or a saturated aliphatic dicarboxylic acid containing from 3 to 8 carbon atoms, the molar ratio between the polyalkylenepolyamine and the dicarboxylic acid being from 0.8:1 to 1.4:1, the thus produced polyamino amide subsequently being reacted with epichlorohydrin in a molar ratio of epichlorohydrin to the secondary amine groups in the polyaminoamide of from 0.5:1 to 1.8:1;
(9) a cyclopolymer which is a homopolymer comprising repeat units of formulae (IX) or (IX')

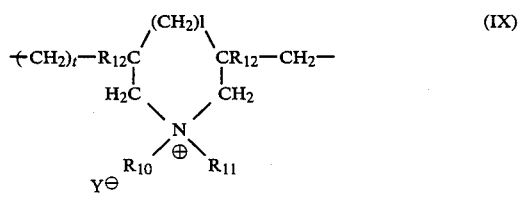

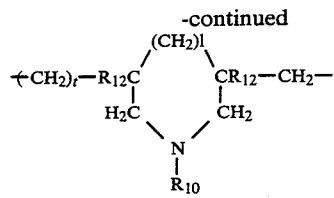

in which l and t are 0 to 1 and the sum l+t is 1, $R_{12}$ is hydrogen or a methyl group, $R_{10}$ and $R_{11}$ are each, independently of each other, an alkyl group containing from 1 to 22 carbon atoms, a hydroxyalkyl group or a lower amidoalkyl group, $R_{10}$ and $R_{11}$, together with the nitrogen atom to which they are attached, are a heterocyclic group, and $Y^\ominus$ is an anion, or a copolymer comprising units of formula (IX) or (IX') and units derived from acrylamide or diacetoneacrylamide;

(10) a quaternary ammonium polymer comprising recurrent repeat units of formula:

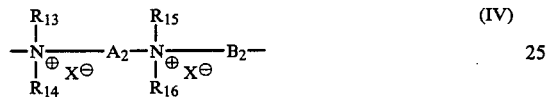

in which $R_{13}$, $R_{14}$, $R_{15}$ and $R_{16}$ are each, independently of each other, an aliphatic, alicyclic or arylaliphatic group containing from 1 to 20 carbon atoms or a lower aliphatic hydroxyalkyl group; or $R_{13}$ and $R_{14}$ and $R_{15}$ and $R_{16}$ together or separately form, with the nitrogen atoms to which they are attached, a heterocyclic ring which optionally contains a second heteroatom other than nitrogen; or $R_{13}$, $R_{14}$, $R_{15}$ and $R_{16}$ are each, independently of each other, a linear or branched $C_2$–$C_6$ alkyl group substituted by a nitrile, ester, acyl, amide or

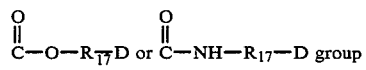

in which $R_{17}$ is an alkylene group and D is a quaternary ammonium group and $A_2$ and $B_2$ are each, independently of each other, a polymethylenic group containing from 2 to 20 carbon atoms which is linear or branched, saturated or unsaturated and which optionally contains, linked to or inserted into the main chain, one or more aromatic rings or one or more oxygen or sulphur atoms or SO, $SO_2$, disulphide, amino, alkylamino, hydroxyl, quaternary ammonium, ureido, amide or ester groups; or $A_2$ and $R_{13}$ and $R_{15}$ may form, with the two nitrogen atoms to which they are attached, a piperazine ring; and when $A_2$ is a linear or branched, saturated or unsaturated alkylene or hydroxyalkylene radical, $B_2$ may also be a group of formula:

$$-(CH_2)_n-CO-D-OC-(CH_2)_n-$$

in which D is (a) a glycol residue of formula $-O-Z-O-$ in which Z is a linear or branched hydrocarbon group or a group of formula:

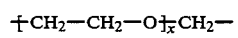

or

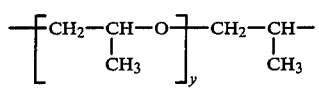

in which x or y is an integer from 1 to 4 representing a specified and unique degree of polymerization or any number from 1 to 4 representing an average degree of polymerization; or (b) a residue of a bis-secondary diamine;

(c) a residue of a bis-primary diamine of formula:

$$-NH-Y-NH-$$

in which Y is a linear or branched hydrocarbon group or a divalent group of formula:

$$-CH_2-CH_2-S-S-CH_2-CH_2$$

(d) a ureylene group of formula:
$$-NH-CO-NH-$$

(11) a quaternary polyammonium polymer comprising units of formula:

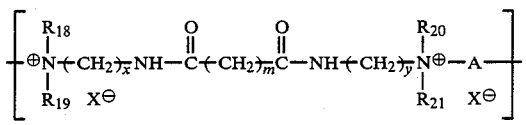

in which $R_{18}$, $R_{19}$, $R_{20}$ and $R_{21}$, are each, independently of each other, hydrogen or a methyl, ethyl, propyl, $\beta$-hydroxyethyl, $\beta$-hydroxypropyl or $-CH_2CH_2(OCH_2CH_2)_pOH$ group in which p is an integer of from 0 to 6, with the proviso that $R_{18}$, $R_{19}$, $R_{20}$ and $R_{21}$ are not simultaneously hydrogen, x and y are each, independently of each other, integers of from 1 to 6, m is an integer of from 0 to 34, X is a halogen and A is the residue of a dihalide;

(12) a homopolymer or copolymer derived from acrylic or methacrylic acid comprising units of formula:

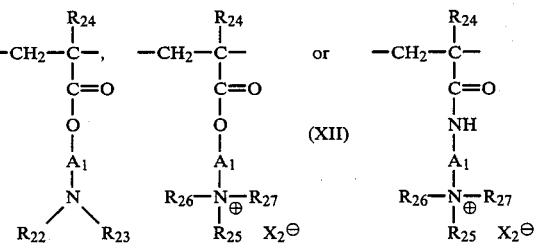

in which $R_{24}$ is hydrogen or a methyl group, $A_1$ is a linear or branched alkyl group containing from 1 to 6 carbon atoms or a hydroxyalkyl group containing 1 to 4 carbon atoms, $R_{25}$, $R_{26}$ and $R_{27}$ are each, independently of each other, an alkyl group containing from 1 to 18 carbon atoms or a benzyl group, $R_{22}$ and $R_{23}$ are each, independently of each other, hydrogen or an alkyl group containing from 1 to 6 carbon atoms, and $X_2^\ominus$ is a methosulphate anion or a halide anion;

(13) a quaternary vinylpyrrolidone or vinylimidazole polymer; or

(14) a polyalkyleneimine, vinylpyridine or vinylpyridinium polymer, a condensate of a polyamine with epichlorohydrin, a quaternary polyureylene or a chitin derivative.

25. A composition according to claim 24 in which the cationic polymer is as defined in paragraph (9) therein wherein $R_{10}$ and $R_{11}$ are each, independently of each other, a hydroxyalkyl group in which the alkyl moiety contains from 1 to 5 carbon atoms or is as defined in paragraph (10) therein wherein D is a residue of a piperazine derivative.

26. An aerosol device for the treatment of the hair or the skin comprising an aerosol container containing in the form of one delayed-foaming gel, a composition which consists essentially of one surface-active, one heterobiopolysaccharide, one delayed-foaming agent which is able to form a foam after the composition is spread on the hair or the skin and, as a propellant agent, one condensable gas which is a halogenated or unhalogenated hydrocarbon or mixture thereof with a noncondensable gas, in a cosmetically acceptable medium.

27. A device according to claim 26 which contains a jacket with a diaphragm.

28. An aerosol device for the treatment of the hair or the skin comprising an aerosol container containing, in the form of one delayed-foaming gel, a composition which consists essentially of one surface-active agent, one heterobiopolysaccharide, one delayed-foaming agent which is able to form a foam after the composition is spread on the hair or the skin and, as a propellant agent, one noncondensable gas which is insoluble in the composition when under pressure, in a cosmetically acceptable medium.

29. A device according to claim 28 wherein the noncondensable propellant is situated in the upper part of the aerosol and the device is equipped with a dip tube so as to expel the composition under pressure through the dip tube.

30. An aerosol device for the treatment of the hair or of the skin comprising an aerosol container containing, in the form of a delayed-foaming gel, a composition which consists essentially of one surface-active agent, one heterobiopolysaccharide, one delayed-foaming agent in a cosmetically acceptable medium, and one cosmetically useful cationic polymer containing primary, secondary, tertiary and/or quaternary amine groups, having a molecular weight of from 500 to 5,000,000 which is able to form a foam after the composition is spread on the hair or the skin and, as a propellant agent, one condensable gas which is a halogenated or unhalogenated hydrocarbon or mixture thereof with a noncondensable gas, in a cosmetically acceptable medium.

* * * * *